United States Patent
Kodaira

(10) Patent No.: US 9,808,212 B2
(45) Date of Patent: Nov. 7, 2017

(54) MEDICAL COUCH APPARATUS

(71) Applicant: Toshiba Medical Systems Corporation, Otawara-shi (JP)

(72) Inventor: Yasuo Kodaira, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 119 days.

(21) Appl. No.: 14/457,271

(22) Filed: Aug. 12, 2014

(65) Prior Publication Data

US 2014/0345054 A1    Nov. 27, 2014

Related U.S. Application Data

(63) Continuation of application No. PCT/JP2013/076747, filed on Oct. 1, 2013.

(30) Foreign Application Priority Data

Oct. 2, 2012   (JP) ................ 2012-220791

(51) Int. Cl.
    *A61G 7/00*      (2006.01)
    *A61B 6/04*      (2006.01)
    (Continued)

(52) U.S. Cl.
    CPC ............... *A61B 6/04* (2013.01); *A61B 6/547* (2013.01); *A61G 7/103* (2013.01); *A61B 6/0457* (2013.01)

(58) Field of Classification Search
    CPC ....................................................... A61G 7/00
    (Continued)

(56) References Cited

U.S. PATENT DOCUMENTS

| 4,613,122 A | 9/1986 | Manabe |
| 6,769,145 B1 * | 8/2004 | Pfeuffer ............... A61B 6/0442 378/209 |

FOREIGN PATENT DOCUMENTS

| CN | 2889175 Y | 4/2007 |
| JP | 06-014919 A | 1/1994 |

(Continued)

OTHER PUBLICATIONS

Combined Office Action and Search Report dated Jan. 22, 2016 in Chinese Patent Application No. 201380017913.8 with English translation of category of cited documents.

(Continued)

*Primary Examiner* — Fredrick Conley
(74) *Attorney, Agent, or Firm* — Oblon, McClelland, Maier & Neustadt, L.L.P.

(57) ABSTRACT

Medical couch apparatus is provided capable of reducing the overrun amount even if the overrun occurs while shortening the stop distance when the top is urgently stopped to make it difficult for the overrun to occur. The frame is arranged between the couch body and the top to be guided in the rostrocaudal direction of the subject by the couch body. The driving unit transfers the top in the rostrocaudal direction via the frame. The guide unit is arranged between the frame and the top to guide the top in the rostrocaudal direction. The biasing mechanism biases the top in the opposite direction of the transfer direction of the top. The bias control unit applies the force to the top to be transferred in the opposite direction for the frame through the biasing force by the biasing mechanism when the transfer of the top by the driving unit is stopped.

7 Claims, 15 Drawing Sheets

(51) Int. Cl.
  *A61G 7/10*     (2006.01)
  *A61B 6/00*     (2006.01)
(58) Field of Classification Search
  USPC .............................. 5/601, 81.1 HS, 610–611
  See application file for complete search history.

(56) References Cited

FOREIGN PATENT DOCUMENTS

| JP | 7-100131 A | 4/1995 |
| JP | 08-098832 A | 4/1996 |
| JP | 2007-125241 A | 5/2007 |
| JP | 4716850 B2 | 7/2011 |

OTHER PUBLICATIONS

International Search Report dated Dec. 3, 2013 for PCT/JP2013/076747 filed on Oct. 1, 2013 with English Translation.

\* cited by examiner

X2 ←→ X1

X2 ←——→ X1

MEDICAL COUCH APPARATUS

CROSS-REFERENCE TO RELATED APPLICATION

This application is based upon and claims the benefit of priority from Japanese Patent Applications No. 2012-220791 filed on Oct. 2, 2012; the entire contents of which are incorporated herein by reference.

FIELD

The embodiments relate to a medical couch apparatus.

BACKGROUND

Medical couch apparatuses have a couch body, a top having a subject mounted thereon, and a driving unit. The couch body includes a linear guide for guiding the top in the rostrocaudal direction. In addition, the couch body includes a pinion. The top includes a rack which slides so as to mesh with the pinion. The driving unit transfers the top in the rostrocaudal direction by rotating the pinion using a motor as a power source (for example, Patent Document 1). Further, the rostrocaudal direction is sometimes referred to as the Z direction. In addition, one direction of the rostrocaudal direction is sometimes referred to as the Z1 direction, while the other rostrocaudal direction is sometimes referred to as the Z2 direction.

A power sequence circuit is provided to control the power source supplied to the motor, or the like. The power sequence circuit includes a relay. Further, an operation switch is provided for preventing the power source from being supplied to the motor. The operation switch is sometimes referred to as an emergency stop switch.

If the operation switch is operated during transfer of the top in the rostrocaudal direction by the motor, the power source supplied to be provided to the motor is interrupted through the operation of the relay in the power sequence circuit, and the top is braked to stop by the retention of the motor.

Hereinafter, the relation between the transfer velocity (constant velocity) at the time that the top is transferring and the distance until the top is stopped after operating the operation switch will be described with reference to FIG. 11.

FIG. 11 is a view showing the relation between the transfer velocity and the stop distance of the top as a comparative example.

The transfer distance of the top until the top is stopped after operating the operation switch during transfer of the top is sometimes referred to as a stop distance or an emergency stop distance, the transfer distance of the top during an idle running time until the top is braked after operating the operation switch is sometimes referred to as an idle running distance, and the transfer distance of the top during the braking time until the top is stopped after braking is sometimes referred to as a braking distance. The idle running time is generated due to the response delay time until the power source supplied to the motor is interrupted after operating the operation switch, as the relay of the power sequence circuit undergoes an operation delay. The idle running distance is generated as the motor is rotated and the top is transferred during the response delay time.

FIG. 11 depicts the idle running time [sec] as "$t_1$" and the braking time [sec] as "$t_2$." In addition, FIG. 11 illustrates a velocity diagram shown by a bold line with the transfer velocity (constant velocity) [mm/s] defined as "V" when the top is transferred. Further, the stop distance [mm] at the velocity V is represented as "d," the idle running distance [mm] is represented as "$d_1$," and the braking distance [mm] is represented as "$d_2$."

Thereby, the $d_1$ and $d_2$ are represented respectively by the following formulas.

$$d_1 = V \cdot t_1 \quad (2)$$

$$d_2 = V \cdot t_2/2 \quad (3)$$

The stop distance d is obtained by adding the idle running distance $d_1$ and the control distance $d_2$, and it makes the d to be represented by the following formula using the formulas (2), (3).

$$d = V \cdot t_1 + V \cdot t_2/2 \quad (4)$$

Recently, speeding up for transferring the top at high velocities has been promoted. FIG. 11 illustrates a velocity diagram shown by a bold dashed line when the top is transferred at high velocities. FIG. 11 depicts the velocity when the top is transferred at high velocities as "$V_h$," the stop distance [mm] as "$d_h$," the idle running distance [mm] as "$d_3$," and the braking distance [mm] as "$d_4$." Further, it is assumed that the force to brake the top (braking force) is the same at the velocity V and at the high velocity $V_h$. Accordingly, the control time at the high velocity $V_h$ becomes twice the braking time $t_2$ at the velocity V ($2t_2$.)

Thereby, the $d_3$, $d_4$, and $d_h$ are respectively represented by the following formulas.

$$d_3 = V_h \cdot t_1 \quad (5)$$

$$d_4 = V_h \cdot 2t_2 \quad (6)$$

$$d_h = V_h \cdot t_1 + V_h \cdot 2t_2 \quad (7)$$

Here, assuming that the high velocity $V_h$ is twice the velocity V, the $V_h$ and $d_h$ are represented by the following formulas.

$$V_h = 2V \quad (8)$$

$$d_h = 2V \cdot t_1 + 2V \cdot t_2 \quad (9)$$

The following formula is established from the formula (9).

$$d_h = 2d + V \cdot t_2 \quad (10)$$

It is known from the formula (10) that the stop distance becomes double or more if the top is transferred at twice the velocity.

Generally, the higher the transferring velocity of the top becomes, the longer the stop distance becomes. Further, it is sometimes referred to as an overrun when the top exceeds a specific distance, while the amount by which the top exceeds the specific distance is sometimes referred to as the overrun amount.

Even if the top is transferred at high velocities, in terms of ensuring safety, it is necessary to stop the top within the specific distance.

However, the higher the transferring velocity of the top becomes, the longer the stop distance becomes in conventional medical couch apparatuses, therefore, it has been necessary to set a limit value to the highest velocity of the top in order to stop the top within the specific distance. Setting no limitation value to the highest velocity has been problematic in that the overrun easily occurs.

DETAILED DESCRIPTION

The embodiments solve the abovementioned problem, with the object intended to provide a medical couch apparatus capable of reducing the overrun amount even if the overrun occurs while shortening the stop distance when the top is urgently stopped to make it difficult for the overrun to occur.

To solve the abovementioned problem, the medical couch apparatus of this embodiment comprises: a couch body; a top; a frame; a driving unit; a guide unit; a biasing mechanism; and a bias control unit. On the top, subject is mounted. The frame is arranged between the couch body and the top to be guided in the rostrocaudal direction of the subject by the couch body. The driving unit transfers the top in the rostrocaudal direction via the frame. The guide unit is arranged between the frame and the top and configured to guide the top in the rostrocaudal direction. The biasing mechanism biases the top in the opposite direction of the transfer direction of the top. The bias control unit applies the force to the top to be transferred in the opposite direction for the frame through the biasing force by the biasing mechanism when the transfer of the top by the driving unit is stopped.

First Embodiment

A first embodiment of the medical couch apparatus will be described with reference to each drawing.

Figure 1:
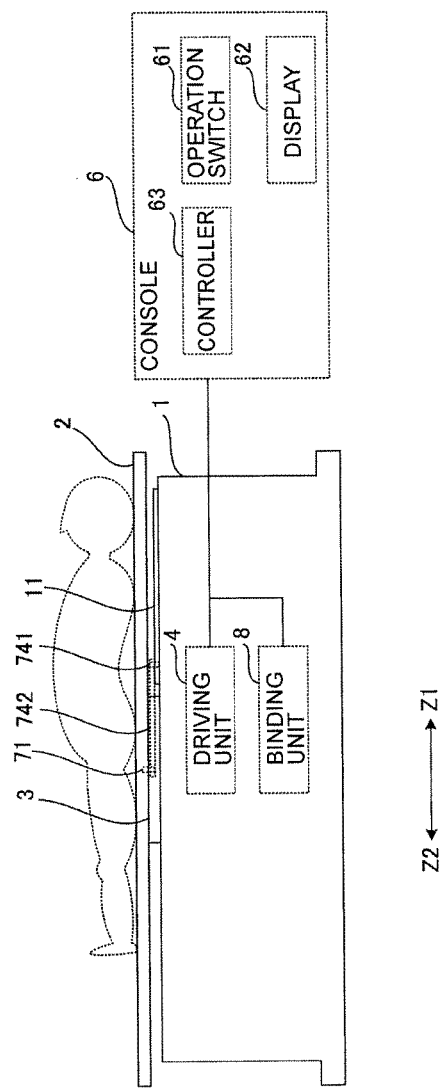
FIG. 1 is an overall view of a medical couch apparatus according to a first embodiment.
Figure 2:
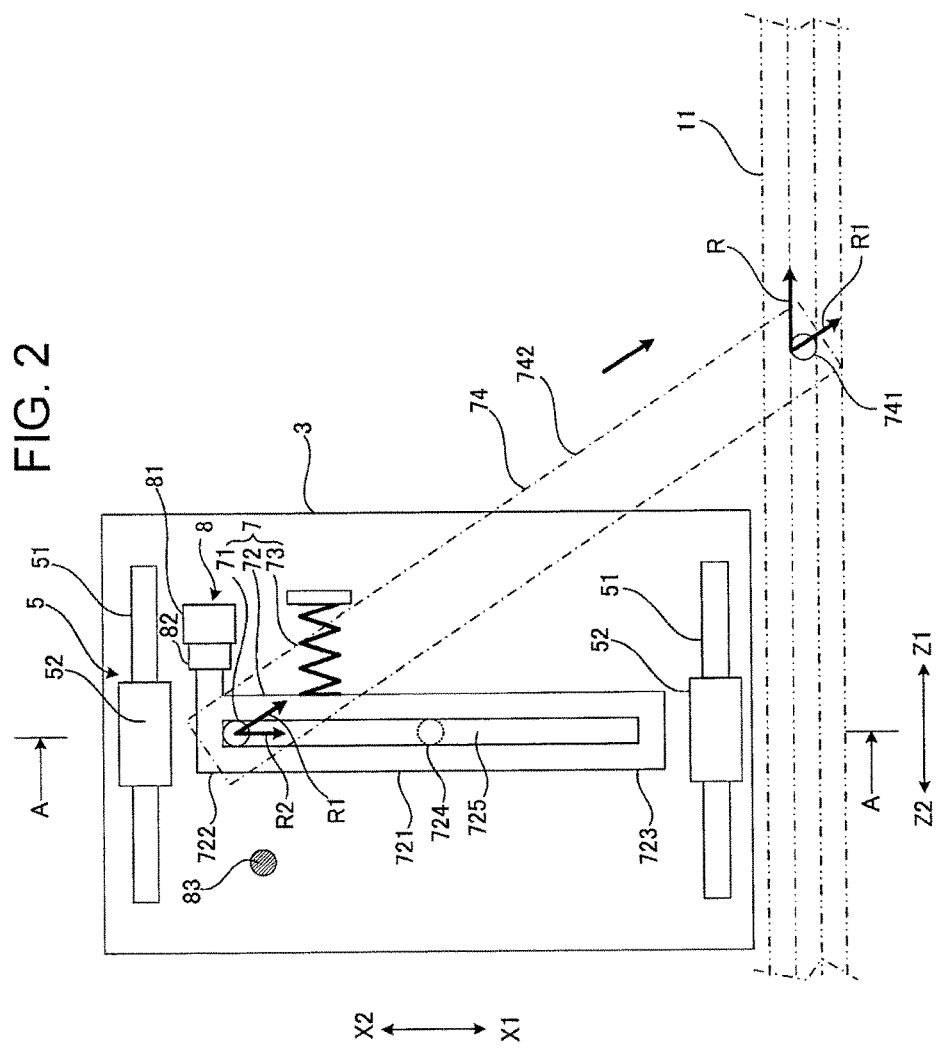
FIG. 2 is a partial plan view top illustrating a biasing mechanism when a top is biased in the Z2 direction.
Figure 3:
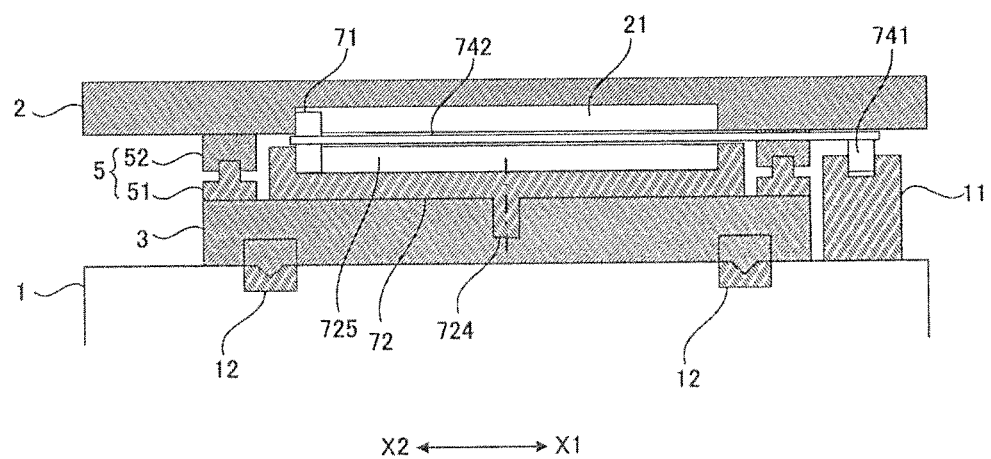
FIG. 3 is a sectional view taken along line A-A of FIG. 2.

FIG. 1 is an overall view of the medical couch apparatus, FIG. 2 is a partial plan view illustrating a biasing mechanism when a top is biased in the Z2 direction, and FIG. 3 is a sectional view taken along line A-A of FIG. 2. FIG. 1 illustrates a top 2 that is transferred to a position in the Z2 direction.

As illustrated from FIG. 1 to FIG. 3, the medical couch apparatus includes a couch body 1, the top 2, a travel frame 3, a driving unit 4, a guide unit 5, a console 6, a biasing mechanism 7, and a binding unit 8 as a bias control unit which controls the biasing mechanism 7.

As illustrated in FIG. 3, the couch body 1 includes a channel rail 11, guide rails 12, and a rack (illustration omitted.)

As illustrated in FIG. 1, the console 6 includes an input part having an operation switch 61, a display 62, and a controller 63. The controller 63 has a power sequence circuit.

Figure 4:
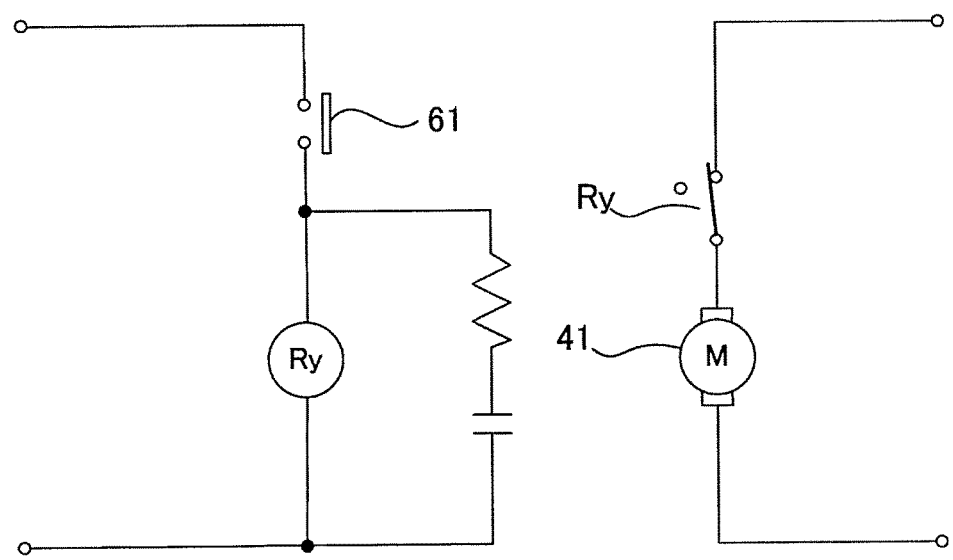
FIG. 4 is a view illustrating a power sequence circuit.

FIG. 4 is a view illustrating the power sequence circuit. As illustrated in FIG. 4, the power sequence circuit having a relay Ry is configured such that the coil of the relay is energized when the operation switch 61 is operated; thereby, a contact point b of the relay is opened to interrupt the power source supplied to a motor 41 of the driving unit 4.

As illustrated in FIG. 2 and FIG. 3, the channel rail 11 has a U-shaped channel sectional shape, which is provided on the couch body 1 in the Z direction.

The guide rails 12, which are provided on the couch body 1, guide the travel frame 3 in the Z direction.

A rack is provided in the couch body 1 in the Z direction, which meshes with the pinion (its illustration omitted) of the driving unit 4.

(Top 2)

Figure 5:
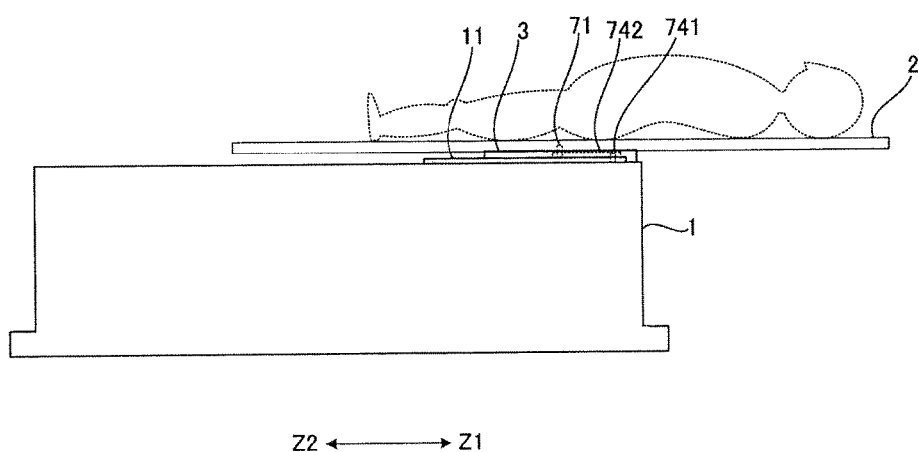
FIG. 5 is a view illustrating a case when the top is transferred to a position in the Z1 direction in the medical couch apparatus.

The top 2 has a subject mounted thereon. FIG. 5 is a view illustrating the case when the top 2 is transferred to the position in a Z1 direction.

As illustrated in FIG. 1 and FIG. 5, the top 2 is provided to the couch body 1 via the travel frame 3. The top 2 is integrally guided with the travel frame 3 by the guide rails 12 (refer to FIG. 3) in the Z direction.

The top 2 has a long hole 21 (refer to FIG. 3) provided in the horizontal direction orthogonal to the Z direction. Further, the horizontal direction orthogonal to the Z direction is sometimes referred to as the X direction. In addition, the right and left directions are sometimes referred to as a direction X1 and a direction X2, respectively, in FIG. 3.

(Travel Frame 3)

As illustrated from FIG. 1 to FIG. 3, the travel frame 3 is arranged between the couch body 1 and the top 2. The travel frame 3 is guided by the guide rails 12 in the Z direction.

(Driving Unit 4)

The driving unit 4 provided for the couch body 1 includes the motor 41 (refer to FIG. 4), a deceleration mechanism (illustration omitted), and the pinion (illustration omitted.) The motor 41 is rotated by being supplied with a power source. The deceleration mechanism decelerates the rotation of the motor 41 to transmit the decelerated rotation to the pinion. The pinion meshes with the rack. For example, if the motor 41 is forward rotated, the pinion rolls in the Z1 direction while meshing with the rack. Thereby, the travel frame 3 is transferred in the Z1 direction. If the motor 41 is backward rotated, the pinion rolls in the Z2 direction while meshing with the rack. Thereby, the travel frame 3 is transferred in the Z2 direction.

(Guide Unit 5)

As illustrated from FIG. 1 to FIG. 3, the guide unit 5 is arranged between the travel frame 3 and the top 2 to guide the top 2 in the Z direction. A LM guide (Linear Motion Guide) is an example of the guide unit 5. The LM guide has LM rails 51 and LM blocks 52. The LM rails 51 are provided to the travel frame 3. The LM blocks 52 are provided to the top 2. The top 2 is relatively guided in the Z direction for the travel frame 3 by sliding the LM blocks 52 along the LM rails 51.

The long hole 21 is arranged on the top 2 between a pair of the LM blocks 52 on opposite sides as illustrated in FIG. 3. A transferring member 71 arranged between the top 2 and a link member 72 is transferably engaged with the long hole 21 while being transferably engaged with a guide hole 725.

In other words, the top 2 is integrally guided with the travel frame 3 by the guide rails 12 in the Z direction while being guided relatively in the Z direction for the travel frame 3 by the guide unit 5.

(Operation Switch 61)

As illustrated in FIG. 4, the operation switch 61 is connected in series with the coil of the relay. If the operation switch 61 is operated, the coil of the relay is energized, opening the contact point b of the relay and interrupting the power source supplied to the motor 41 of the driving unit 4.

(Biasing Mechanism 7)

Figure 6:
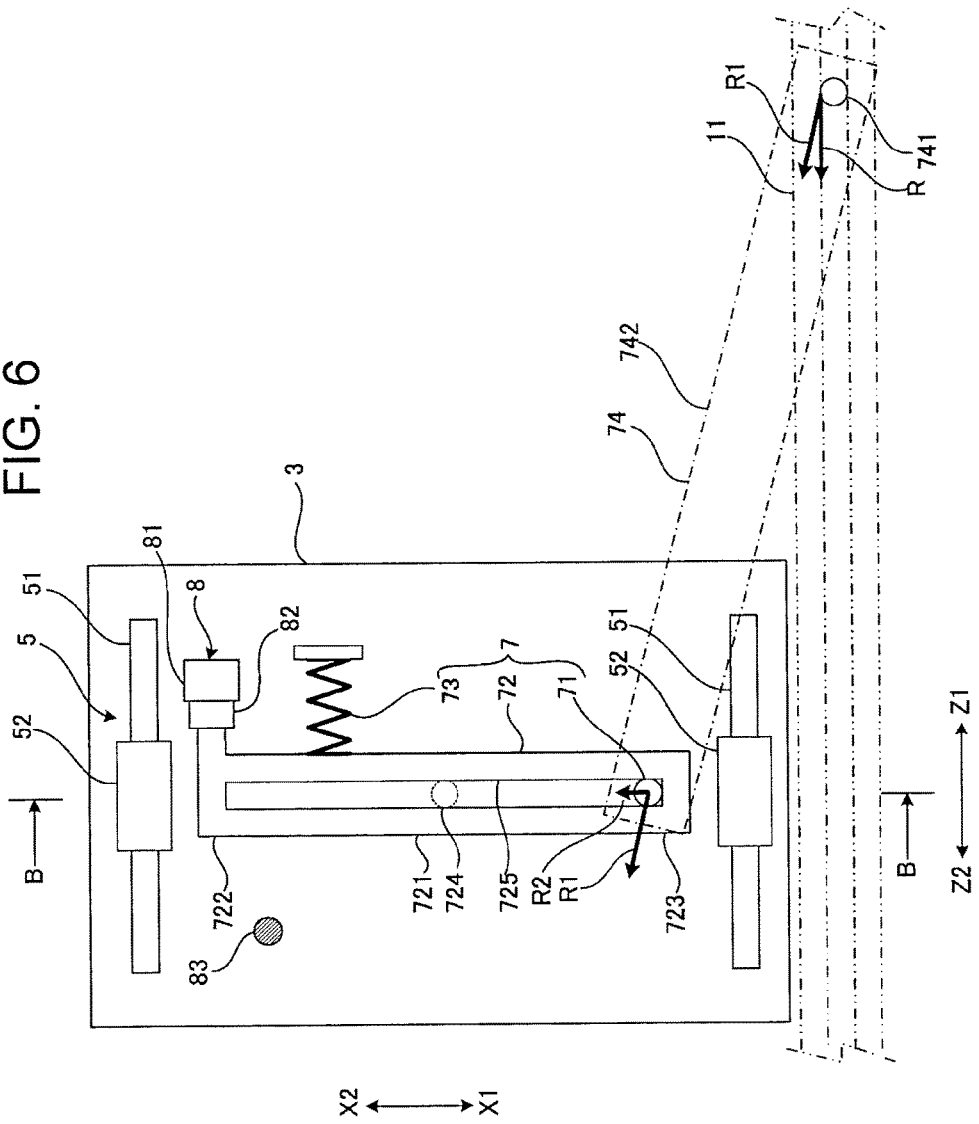
FIG. 6 is a partial plan view illustrating the biasing mechanism when the top is biased in the Z1 direction.
Figure 7:
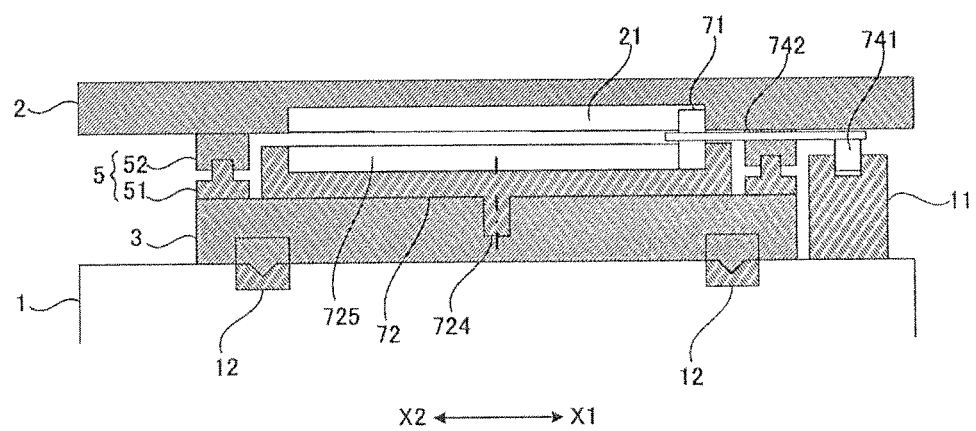
FIG. 7 is a sectional view taken along line B-B of FIG. 6.

Hereinafter, the biasing mechanism 7 will be described with reference to FIG. 2, FIG. 3, FIG. 6, and FIG. 7. FIG. 6 is a partial plan view illustrating the biasing mechanism 7 when the top 2 is biased in the Z1 direction, while FIG. 7 is a sectional view taken along line B-B of FIG. 6.

As illustrated in FIG. 2, FIG. 3, FIG. 6, and FIG. 7, the biasing mechanism 7 includes the transferring member 71, the link member 72, a bias member 73, and a switch unit 74.

As illustrated in FIG. 2 and FIG. 3, the transferring member 71 is a pin having a circular sectional shaped shaft, which is engaged with the long hole 21 of the top 2.

As illustrated in FIG. 2 and FIG. 6, the link member 72 includes a center part 721, a one end 722, and an other end 723. The center part 721 is axially supported on the travel frame 3 by a pivot shaft 724 rotatably. The link member 72 includes the guide hole 725 for guiding the transferring member 71 between the one end 722 and the other end 723 in a reciprocable manner.

The bias member 73 is a compression coil spring, and, by anticlockwise biasing the link member 72, biases the top 2 via the transferring member 71 in the Z2 direction in FIG. 2 and in the Z1 direction in FIG. 6.

As illustrated in FIG. 2, FIG. 3, FIG. 6, and FIG. 7, the switch unit 74 includes an engaging member 741 and a juncture member 742.

The engaging member 741 is a pin having a circular sectional shaped shaft, which is engaged with the channel rail 11 so as to be guided in the Z direction.

The juncture member 742 is formed as a lengthy shape with the transferring member 71 provided on one longitudinal edge portion. The other edge portion of the juncture member 742 is elongated to the channel rail 11, which is provided with the engaging member 741.

When the engaging member 741 transfers along the channel rail 11, the engaging member 741 receives the friction resistance force from the channel rail 11 in the opposite direction of its transfer direction. The switch unit 74 transfers the transferring member 71 to a position between the one end 722 of the link member 72 and the other end 723 of thereof using the friction resistance force received by the engaging member 741 from the channel rail 11 when the top 2 is transferred.

As described above, the switch unit 74 transfers the transferring member 71 via the friction resistance force generated between the engaging member 741 and the channel rail 11.

Hereinafter, the relation between the transfer direction of the top 2 and that of the transferring member 71 will be described with reference to FIG. 2 and FIG. 6.

FIG. 2 illustrates the transferring member 71 positioned at the one end 722 of the link member 72. In this case, the bias member 73 biases the top 2 via the transferring member 71 in the Z2 direction. FIG. 6 illustrates the transferring member 71 positioned at the other end 723 of the link member 72. In this case, the bias member 73 biases the top 2 via the transferring member 71 in the Z1 direction.

The engaging member 741 and the juncture member 742, which are the members used to transfer the transferring member 71, will be described in detail with reference to FIG. 2.

If the travel frame 3 transfers the top 2 via the transferring member 71 in the Z2 direction, the engaging member 741 receives the friction resistance force in the Z1 direction from the channel rail 11. FIG. 2 depicts the friction resistance force in the Z1 direction as "R."

The longitudinal force of the juncture member 742 in the friction resistance force R is transmitted from the juncture member 742 to the transferring member 71. This longitudinal force is depicted as "R1" in FIG. 2. This force R1 becomes a component to transfer the transferring member 71 in the X1 direction. The component is depicted as "R2" in FIG. 2. The transferring member 71 transfers to the position of the other end 723 of the link member 72 from the position of the one end 722 thereof due to the component R2, allowing the bias member 73 to bias the top 2 in the Z1 direction (the direction opposite the transfer direction Z2 of the top 2) via the transferring member 71 (refer to FIG. 6.)

If the top 2 (the travel frame 3) is transferred in the Z1 direction in FIG. 6, the engaging member 741 receives the friction resistance force in the Z2 direction from the channel rail 11. FIG. 6 depicts the friction resistance force in the Z2 direction as "R."

The longitudinal force of the juncture member 742 in the friction resistance force R is transmitted from the juncture member 742 to the transferring member 71. This longitudinal force is depicted as "R1" in FIG. 6. This force R1 becomes a component to transfer the transferring member 71 in the X2 direction. This component is depicted as "R2" in FIG. 6. The transferring member 71 transfers to the position of the one end 722 of the link member 72 from the position of the other end 723 thereof due to this component R2, allowing the bias member 73 to bias the top 2 in the Z2 direction (the direction opposite the transfer direction Z1 of the top 2) via the transferring member 71 (refer to FIG. 2.)

Using the engaging member 741 and the juncture member 742, the engaging member 741 transfers the transferring member 71 to either the position of the one end 722 of the link member 72 or the position of the other end 723 thereof due to the friction resistance force received from the channel rail 11 and in response to the direction of the friction resistance force when the top 2 is transferred, enabling the reliable transfer of the top 2 in the direction opposite the transfer direction for the travel frame 3.

(Binding Unit 8)

Hereinafter, the binding unit 8 will be described with reference to FIG. 2, FIG. 6, and FIG. 8.

As illustrated in FIG. 2 and FIG. 6, the binding unit 8 includes a permanent magnet 82, an electromagnet 81, and a stopper 83. The permanent magnet 82 is fixed to the one end 722 of the link member 72.

The electromagnet 81 is adapted to bind the link member 72 such that the link member is not rotated against the biasing force of the binding unit by being attracted to the permanent magnet 82 when the power source is supplied, and to release the binding when the power source is interrupted. It is possible to return the top 2 in the direction opposite the transfer direction for the travel frame 3 without waiting for the idle running time as the response time until the electromagnet 81 releases the binding of the top 2 after interrupting the power source is short.

Figure 8:
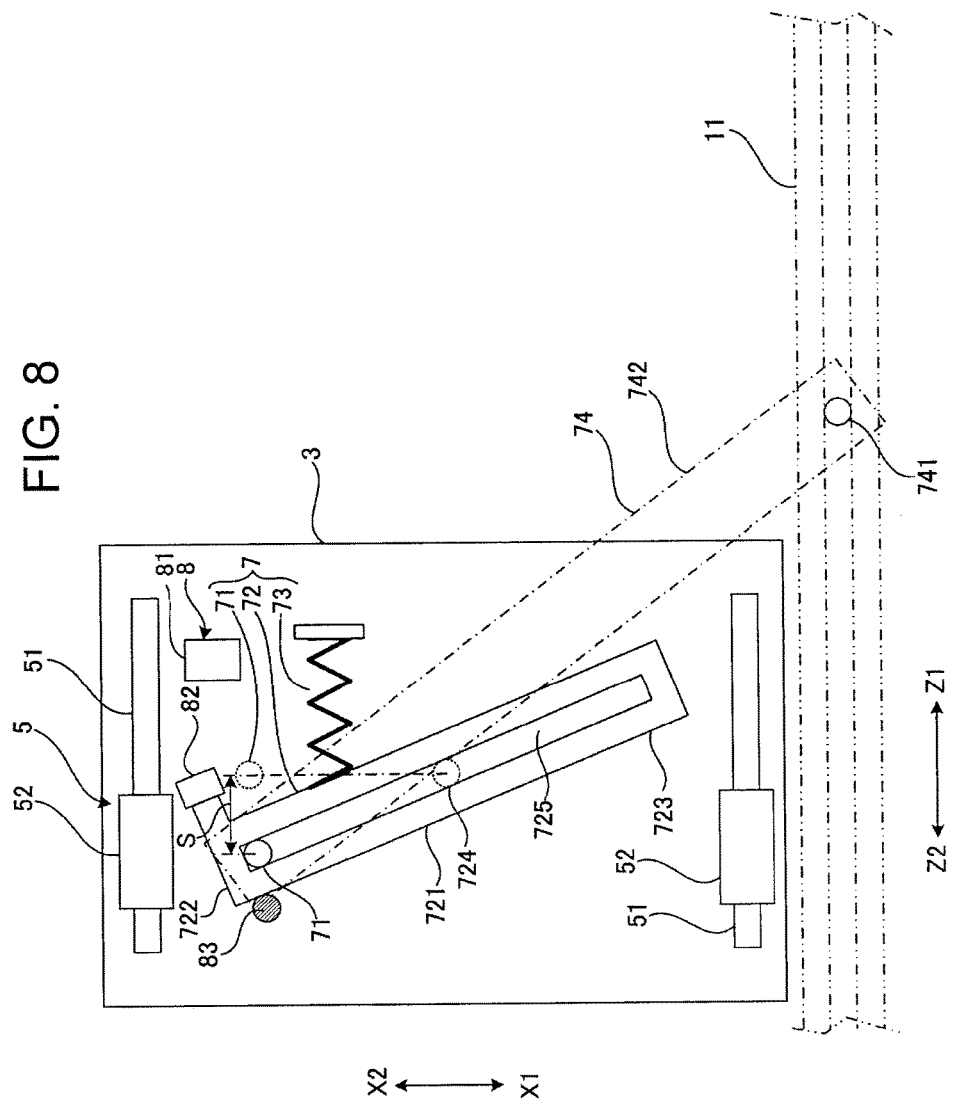
FIG. 8 is a view illustrating a case when the top is transferred in the Z2 direction by the biasing force with the power source interrupted.

FIG. 8 is a view illustrating the case when the top 2 is transferred in the opposite direction (Z2 direction) for the travel frame 3 by the biasing force with the power source interrupted. As illustrated in FIG. 8, the stopper 83 limits the anticlockwise rotation of the link member 72 by coming into contact with the link member 72.

In FIG. 2, the electromagnet 81, which is attracted to the permanent magnet 82 with the power source supplied, binds the link member 72 against the biasing force of the bias member 73 such that the link member 72 is not anticlockwise rotated.

As illustrated in FIG. 8, if the electromagnet 81 is not attracted to the permanent magnet 82 with the power source interrupted, the binding of the link member 72 is released to rotate the link member 72 anticlockwise due to the biasing force. Thereby, the top 2 transfers in the Z2 direction via the transferring member 71. If the link member 72 is rotated anticlockwise, the link member 72 comes into contact with the stopper 83 to limit the anticlockwise rotation.

The difference in the Z direction between the position of the transferring member 71 in FIG. 2 and the position of the transferring member 71 in FIG. 8 becomes the transfer amount by which the top 2 is transferred in the opposite direction for the travel frame 3 (denoted as "S" in FIG. 8).

Hereinafter, an informing unit for demonstrating that the medical couch apparatus is not in the emergency stop corresponding state will be described with reference to FIG. 1, FIG. 2, and FIG. 6.

The informing unit includes the display 62 of the console 6, detecting units, and an informing control unit (illustration omitted.)

The display 62 demonstrates of the presence or absence of the correspondence relation between the transfer direction of the top 2 and the position of the transferring member 71. Here, to have the correspondence relation unit that the transferring member 71 is positioned at the one end 722 of the link member 72 when the top 2 is transferred in the Z1 direction (the first correspondence relation illustrated in FIG. 2) or the transferring member 71 is positioned at the other end 723 of the link member 72 when the top 2 is transferred in the Z2 direction (the second correspondence relation illustrated in FIG. 6). In addition, to have no correspondence relation unit to have neither the first nor the second correspondence relation.

The detecting units are arranged at the position of the one end 722 of the link member 72 and at the position of the other end 723 thereof. The detecting units respectively output respective signals when the transferring member 71 transfers to the position of the one end 722 of the link member 72, and when the transferring member 71 transfers to the position of the other end 723 of the link member 72. Accordingly, it can be determined that the transferring member 71 transfers to neither the one end 722 nor the other end 723 when the detecting units do not output any of the respective signals. Examples of the detecting unit include a limit switch and a proximity sensor.

The informing control unit is configured as a part of the controller 63. The informing control unit determines whether or not the transfer direction of the top 2 and the position of the transferring member 71 have a predetermined correspondence relation upon receiving the signals output from the detecting units and the information regarding the transfer direction of the top 2, making the display 62 demonstrate the presence or absence of the correspondence relation.

Hereinafter, a series of flows from the transfer of the top 2 to the demonstration of the correspondence relation will be described with reference to FIG. 9.

Figure 9:
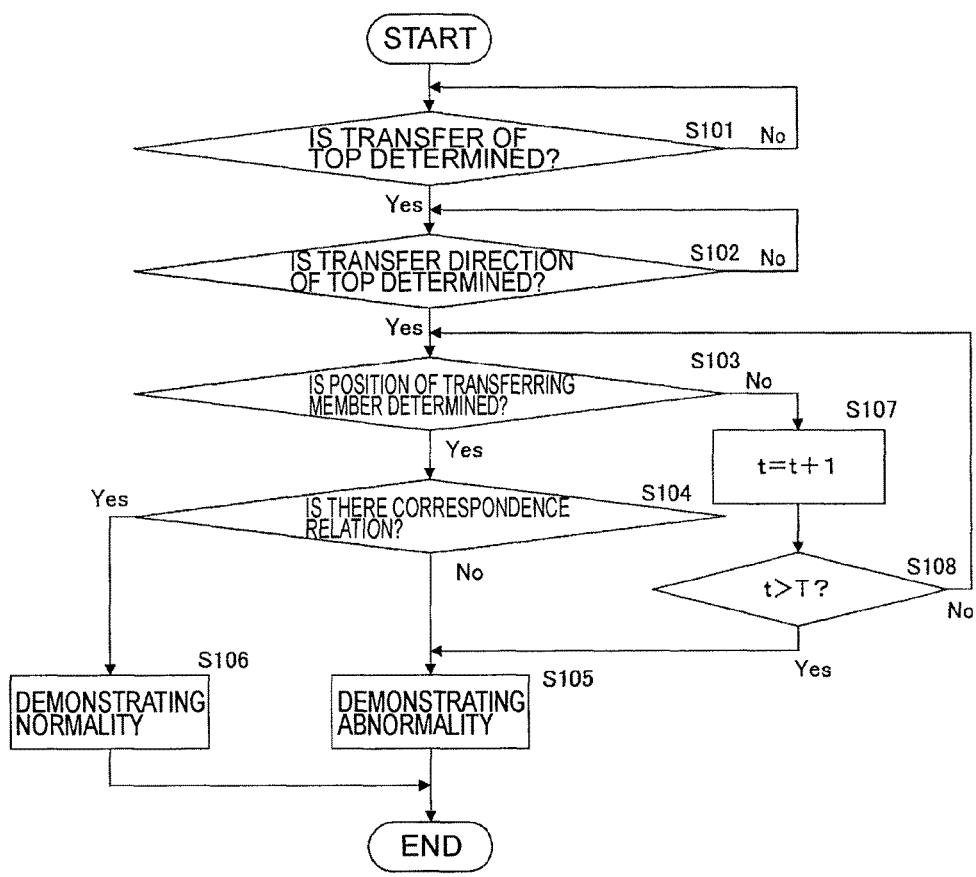
FIG. 9 is a flowchart illustrating a series of flows until the correspondence relation is demonstrated after the top is transferred.

As illustrated in FIG. 9, at first, it is determined whether or not the top 2 is transferring (S101.)

Subsequently, in the case in which transfer of the top 2 is determined (S101: Yes), the transfer direction of the top is determined (S102).

Subsequently, when the transfer direction of the top 2 is determined (S102: Yes), the position of the transferring member 71 is determined (S103). Here, to determine the position of the transferring member 71 refers to determining that, as illustrated in FIG. 2 and FIG. 6, the transferring member 71 transfers to either of the one end 722 or the other end 723. In addition, not to determine the position of the transferring member 71 refers to determining that the transferring member 71 transfer to neither of the one end 722 nor the other end 723.

Subsequently, when the position of the transferring member 71 is determined (S103: Yes), it is determined whether or not the transfer direction of the top 2 and the position of the transferring member 71 have a correspondence relation (S104).

Subsequently, when it is determined that there is no correspondence relation (S104: No), the informing control unit makes the display 62 demonstrate that there is no correspondence relation (demonstrating abnormality) (S105.) If there is no correspondence relation, taking this demonstration as an opportunity, it becomes possible to carry out maintenance and inspection. In addition, it is possible to prevent the top 2 from being operated without having any correspondence relation.

When it is determined that there is a correspondence relation in Step S104 (Yes), the informing control unit makes the display 62 demonstrate that there is a correspondence relation (demonstrating normality) (S106.)

When the position of the transferring member 71 is not determined in Step S103 (No), an elapsed time t is added (t=t+1) (S107).

Subsequently, it is determined whether or not the elapsed time t exceeds a predetermined time T (t>T) (S108).

Subsequently, when it is determined that the elapsed time t exceeds the predetermined time T (S108: Yes), the informing control unit makes the display 62 demonstrate the abnormality (S105). Taking this demonstration as an opportunity, it becomes possible to carry out maintenance and inspection. The maintenance and inspection make it possible to maintain the transferring member 71 so as to be normally operated by figuring out the causes of operational failure, and the like, of the transferring member 71.

When it is determined that the elapsed time t does not exceed the predetermined time T in Step S108 (No), the procedure returns to Step S103 for determining the position of the transferring member 71.

As described above, the position of the transferring member 71 has been determined until the elapsed time t exceeds the predetermined time T for the following reason. For example, in the case that the top 2 is transferred in the Z2 direction after the top 2 is transferred in the Z1 direction and stopped, at the time when the top is transferred in the Z1 direction and stopped, the transferring member 71 is positioned at the one end 722 of the link member 72. Subsequently, immediately after the top is transferred in the Z2 direction, the transferring member 71 does not transfer to the position of the other end 723 of the link member 72 while the transferring member 71 remains at the position of the one end 722 of the link member 72 or in the vicinity thereof.

Such remaining the transferring member 71 is also generated immediately after the top 2 is transferred in the Z1 direction after the top 2 is transferred in the Z2 direction and stopped.

In other words, at the point when there is no correspondence relation between the transfer direction of the top 2 and the position of the transferring member 71 immediately after the direction of the top 2 is changed from the Z1 direction into the Z2 direction, or immediately after the direction of the top 2 is changed from the Z2 direction is changed to the Z1 direction, and if the correspondence relation is determined at this point, even though the transferring member 71 is normally operated, abnormal demonstration is carried out. In contrast, in the case of determining the presence or absence of the correspondence relation at the time when the predetermined time has elapsed, if the transferring member 71 is normally operated, the transferring member 71 transfers to either position (a specific position) of the one end 722 of the link member 72 or the other end 723 thereof, and the normal demonstration is carried out since there is the correspondence relation; on the other hand, if the transferring member 71 is not normally operated for some reason, the transferring member does not transfer to the specific position, and the abnormal demonstration is carried out since there is no correspondence relation.

Further, in a series of flows from the transfer of the top 2 to the demonstration of the correspondence relation, the informing control unit causes the presence or absence of the correspondence relation to be demonstrated; however, the informing control unit may simply cause the position of the transferring member to be demonstrated based on the signals output from the detecting unit. Taking this demonstration as an opportunity, a user continues the operation of the top 2, or requests the maintenance and inspection. In addition, the examiner checks the apparatus before as well as after the maintenance and inspection.

(Operation)

Figure 10:
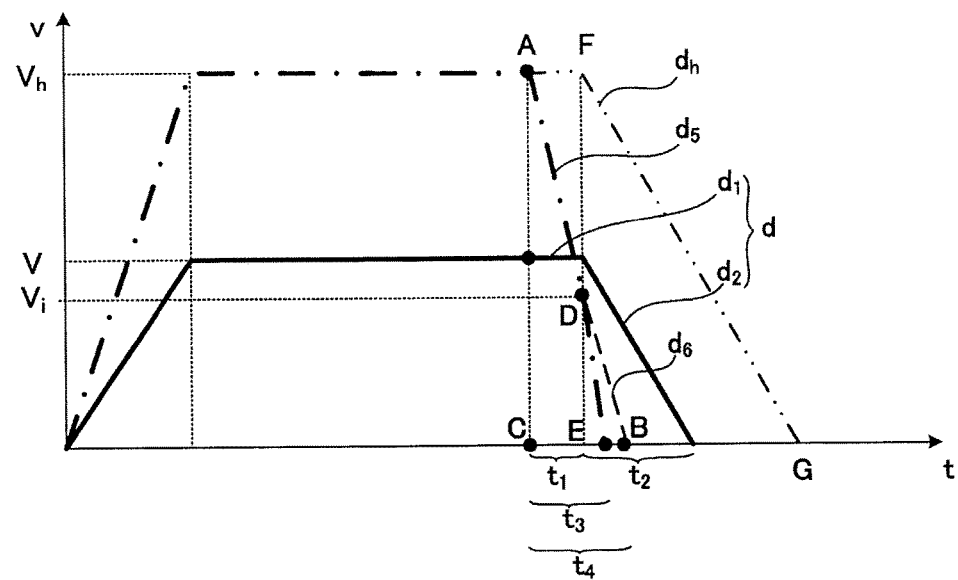
FIG. 10 is a view illustrating an example of the relation between the transfer velocity and the stop distance of the top.
Figure 11:
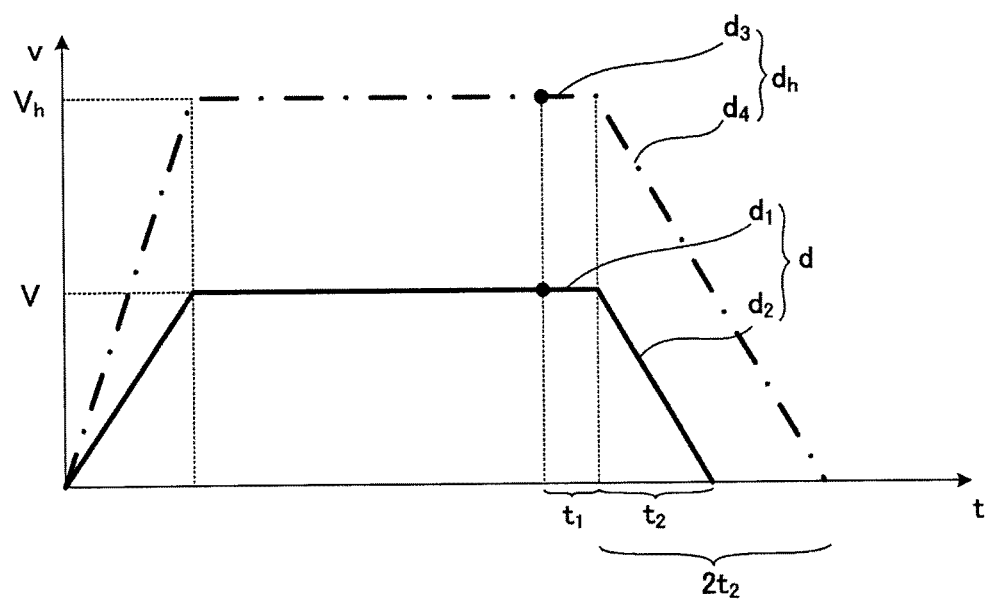
FIG. 11 is a view illustrating a comparative example of the relation between the transfer velocity and the stop distance of the top.

The configuration of the medical couch apparatus has been described as above. Hereinafter, the operation of the medical couch apparatus will be described with reference to FIG. 2, FIG. 6, and FIG. 10. FIG. 10 illustrates an example of the relation between the transfer velocity and the stop distance of the top 2.

During the normal operation of the top 2, the electromagnet 81 attracts the permanent magnet 82 to bind the rotation of the link member 72 (refer to FIG. 2 and FIG. 6).

During the normal operation of the top 2, for example, if the top 2 (the travel frame 3) is transferred in the Z2 direction due to the transfer of the motor 41 in the forward direction, the engaging member 741 receives the friction resistance force in the Z1 direction from the channel rail 11 to transfer the transferring member 71 in the X1 direction via the juncture member 742. Subsequently, the transferring member 71 is positioned at the other end 723 of the link member 72. Thereby, the bias member 73 biases the top 2 in the Z1 direction (the direction opposite the transfer direction Z2 of the top 2) via the transferring member 71.

For example, due to the transfer of the motor 41 in the backward direction, if the top 2 (the travel frame 3) is transferred in the Z1 direction, the engaging member 741 transfers the transferring member 71 in the X2 direction via the juncture member 742 by receiving the friction resistance force in the Z2 direction from the channel rail 11. Subsequently, the transferring member 71 is positioned at the one end 722 of the link member 72. Thereby, the bias member 73 biases the top 2 in the Z2 direction (the direction opposite the transfer direction Z1 of the top 2) via the transferring member 71.

Accordingly, the biasing mechanism 7, when the top 2 is transferred, biases the top 2 in the direction opposite the transfer direction of the top 2.

Hereinafter, an emergency stop time will be described. When the top 2 is transferred in the Z1 direction together with the travel frame 3, if the electromagnet 81 does not attract the permanent magnet 82 with the power source interrupted, the binding of the link member 72 is released, allowing the link member 72 to be rotated anticlockwise by the biasing force (refer to FIG. 8). Thereby, the top 2 is transferred in the Z2 direction for the travel frame 3 via the transferring member 71 positioned at the one end 722 of the link member 72.

Thus, when the top 2 is transferred together with the travel frame 3, if the power source is interrupted, the top 2 is only returned to the travel frame 3 without returning the travel frame 3 in the opposite direction of the transfer direction of the top 2. When the top 2 is urgently stopped by interrupting the power source, the value obtained by subtracting the return amount of the top 2 from the stop distance of the travel frame 3 becomes the stop distance upon urgently stopping the top 2. Compared to the case in which there is no returning amount of the top 2, the stop distance is shortened. Thereby, it is possible to make it difficult to cause an overrun. In addition, even if the overrun is caused, it is also possible to decrease the overrun amount.

In FIG. 10, the velocity diagram when the top 2 is transferred at the high velocity $V_h$ is illustrated by a dashed-dotted line, and the velocity diagram when the top 2 is transferred at the velocity V is illustrated by a solid line, as a comparative example.

For ease of explanation, it is assumed that, upon an emergency stop of the top, the return velocity when the top 2 returns in the opposite direction for the travel frame 3 is constant, and when the travel frame 3 stops, return of the top 2 also ends (the link member 72 comes into contact with the stopper 83). Further, it is assumed that, upon an emergency stop of the top, the transfer velocity of the travel frame 3 is higher than the return velocity of the top 2. Accordingly, when the top 2 is transferred together with the travel frame 3, if an emergency stop is made, the top 2 returns in the opposite direction for the travel frame 3; however, the top 2 transfers in the transfer direction of the travel frame 3.

As illustrated in FIG. 10, when the top 2 is transferred at the high velocity $V_h$, if the power source is interrupted, the travel frame 3 continues to transfer as is at an idle running time $t_1$; however, the top 2 returns in the opposite direction of the transfer direction for the travel frame 3 without waiting for the idle running time $t_1$. The velocity of the top 2 at this time becomes the value obtained by subtracting the returning velocity of the top 2 from the transfer velocity of the travel frame 3. Accordingly, the transfer velocity of the top 2 is decelerated (deceleration at the first stage).

If the idle running time $t_1$ has elapsed, the transfer velocity of the travel frame 3 is decelerated by braking the travel frame 3 due to the retention of the motor 41. At this time, the top 2 also continues to return in the direction opposite the transfer direction for the travel frame 3. The velocity of the top 2 at this time becomes the value obtained by subtracting the returning velocity of the top 2 from the transfer velocity of the travel frame 3 (the decelerated velocity). Accordingly, the velocity of the top 2 is further decelerated (deceleration at the second stage), and the top 2 is then stopped.

In FIG. 10, a time "$t_3$" which is the time until the top 2 is stopped via the first and second decelerations after the power source is interrupted is illustrated. In addition, a stop distance "$d_5$" when the first and second decelerations are made is illustrated.

In FIG. 10, a time "$t_4$" which is the time until the top 2 is stopped only via the first deceleration after the power source is interrupted is illustrated as a comparative example. In addition, the velocity diagram when only the first deceleration is made is illustrated by a broken-line. Further, a stop distance "$d_6$" when only the first deceleration made is illustrated.

The $d_6$ is represented by the following formula.

$$d_6 = V_h \cdot t_4 / 2 \tag{11}$$

This corresponds to the area of a triangle ABC illustrated in FIG. 10.

Assuming that the velocity when the second deceleration is made (during lapse of the $t_1$) is defined as $V_1$, the $d_5$ corresponds to a rectangle ADEC illustrated in FIG. 10. This is the value obtained by subtracting the area of a triangle DBE illustrated in FIG. 10 from the area of the triangle ABC.

In other words, the $d_5$ is represented by the following formula.

$$d_5 = d_6 - (V_1(t_4 - t_3)/2) \tag{12}$$

The stop distance $d_5$ becomes the stop distance of the top 2 upon the emergency stop when the top 2 is transferred at a high velocity.

FIG. 10 illustrates, as a comparative example, the velocity diagram when the top 2 is transferred at the high velocity $V_h$ by a dashed-two dotted line. In addition, a stop distance $d_h$ at that time is represented by the abovementioned formula (7). The $d_h$ corresponds to the area of a rectangle AFGC illustrated in FIG. 10.

Comparing the stop distances $d_5$ and $d_h$ with each other, it is found that the stop distance $d_5$ is largely shortened. Accordingly, it becomes hard to cause an overrun. In addition, even if the overrun is caused, it is possible to decrease the overrun amount.

The case in which an emergency stop is made when the top 2 is transferred in the Z1 direction at a high velocity has been described above, which applies when the top 2 is transferred in the Z2 direction at a high velocity as well. In other words, when the top 2 is transferred in the Z2 direction, if the electromagnet 81 does not attract the permanent magnet 82 with the power source interrupted, the binding of the link member 72 is released, causing the link member 72 to be rotated anticlockwise by the biasing force. Thereby, the top 2 transfers in the Z1 direction (the direction opposite transfer direction Z2 of the top) for the travel frame 3 via the transferring member 71 positioned at the other end 723 of the link member 72. Thereby, the stop distance of the top 2 is shortened, making it possible for an overrun to be hardly caused.

Second Embodiment

Hereinafter, a second embodiment of the medical couch apparatus will be described with reference to FIG. 12. In the second embodiment, differences in the configuration from the first embodiment will be mainly described, with explanations of overlapping configurations omitted.

The biasing mechanism 7 of the first embodiment includes the engaging member 741 and the juncture member 742, while the biasing mechanism 7 of the second embodiment includes an actuator 743 and a control unit.

Figure 12:
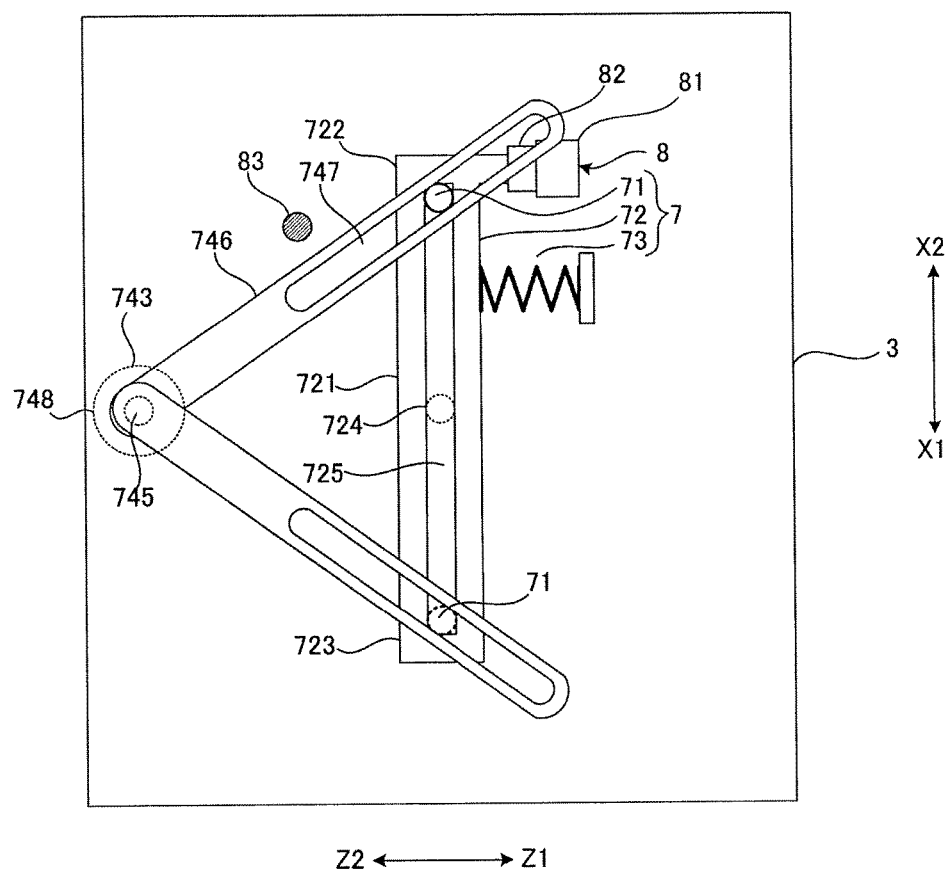
FIG. 12 is a partial plan view illustrating a biasing mechanism according to a second embodiment.

FIG. 12 is a partial plan view illustrating the biasing mechanism 7. As illustrated in FIG. 12, the actuator 743 includes an arm 746 and a prime mover 748. A rotating shaft 745 of the prime mover 748 is coupled to a base end of the arm 746. A guide hole 747 is arranged on the front end of the arm 746. The transferring member 71 is engaged with the guide hole 747 to be guidable.

If the biasing mechanism 7 rotates the arm 746 clockwise by the prime mover 748 using the rotating shaft 745 as a shaft, the transferring member 71 is transferred to the other end 723 of the link member 72 along the guide hole 747, the top 2 is biased in the Z1 direction via the transferring member 71, while, if the biasing mechanism 7 rotates the arm 746 anticlockwise, the transferring member 71 is transferred to the one end 722 of the link member along the guide hole 747, and the top 2 is biased in the Z2 direction via the transferring member 71.

The control unit is configured as a part of the controller 63. The control unit, upon receiving the information when the top 2 (the travel frame 3) is transferred in the Z1 direction, controls the actuator 743 so as to transfer the transferring member 71 to the one end 722 of the link member 72 by transferring the transferring member 71 in the X2 direction. In addition, the control unit, upon receiving the information when the top 2 is transferred in the Z2 direction, controls the actuator 743 so as to transfer the transferring member 71 to the other end 723 of the link member 72 by transferring the transferring member 71 in the X1 direction.

Further, in the second embodiment along with the first embodiment, by providing the detecting unit to output signals in response to the position of the transferring member 71, the position of the transferring member 71 may be demonstrated by the display 62 based on these signals.

According to the second embodiment, it becomes possible to reliably transfer the top 2 in the direction opposite the transfer direction for the travel frame 3, upon an emergency stop when the power source is interrupted, by transferring the transferring member 71 to a specific position with the actuator 743 before the power source is interrupted. It becomes also possible to reliably transfer the top 2 in the direction opposite the transfer direction for the travel frame 3 due to the simple configuration in which the position of the transferring member 71 can be easily transferred on the link member 72 in response to the transfer direction of the top 2 without need for the channel rail 11 and the juncture member 742 of the first embodiment.

Third Embodiment

Subsequently, a third embodiment of the medical couch apparatus will be described with reference to FIG. 13, FIG. 14, and FIG. 15. Further, in the third embodiment 3, differences in the configuration from the first embodiment will be mainly described, with explanations of overlapping configurations omitted.

The biasing mechanism 7 of the first embodiment includes the engaging member 741 and the juncture member 742, while the biasing mechanism 7 of the third embodiment 3 includes the actuator 743, a circular disc member 9, and a control unit. Further, the control unit is configured as a part of the controller.

Figure 13:
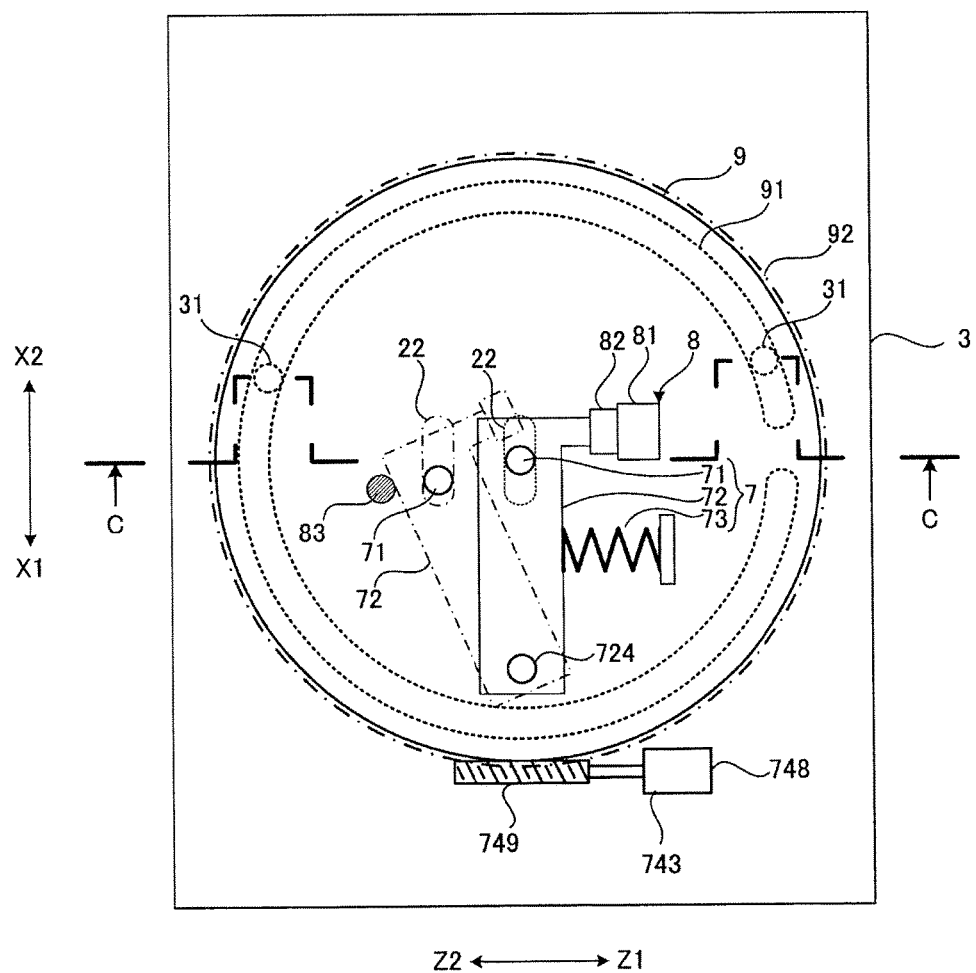
FIG. 13 is a view illustrating a case when the top is biased in the Z2 direction in the biasing mechanism according to a third embodiment.

FIG. 13 is a view illustrating a case when the top 2 is biased in the Z2 direction in the biasing mechanism 7, FIG.

Figure 15:
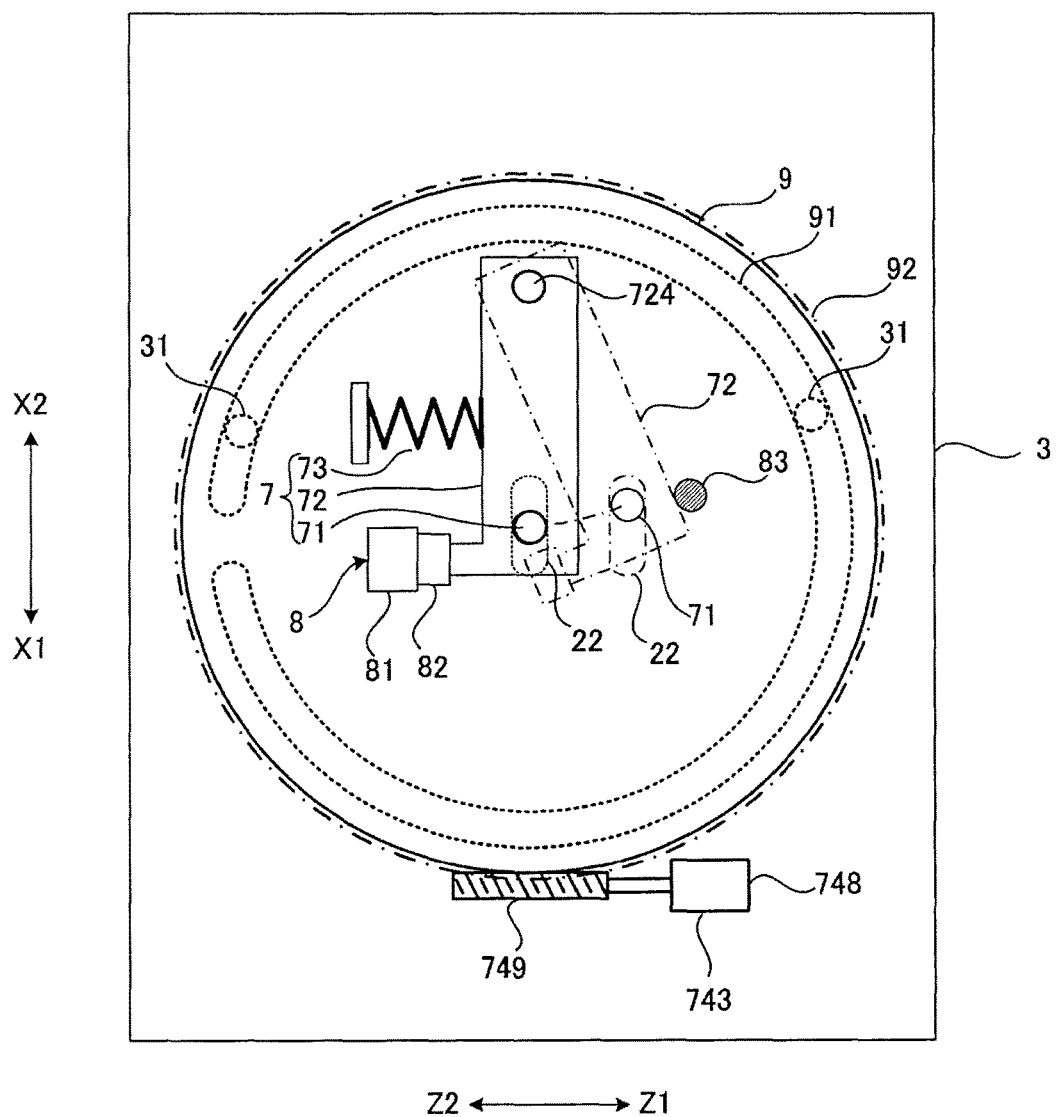
FIG. 15 is a view illustrating a case when the top is biased in the Z1 direction.

14 is a sectional view taken along C-C of FIG. 13, and FIG. 15 is a view illustrating a case when the top 2 is biased in the Z1 direction.

(Actuator)

Figure 14:
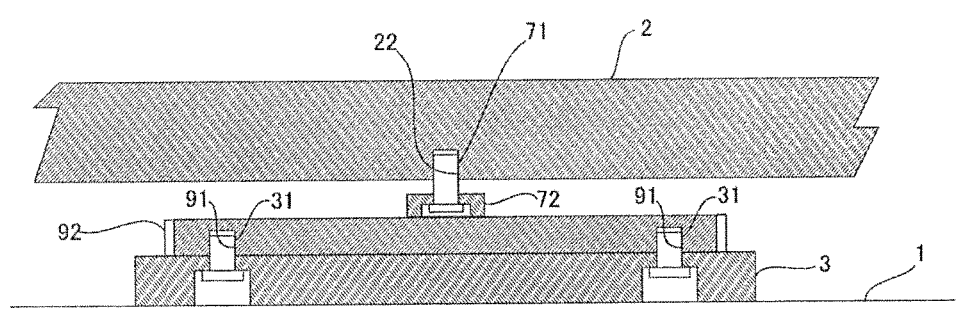
FIG. 14 is a sectional view taken along line C-C of FIG. 13.

As illustrated in FIG. 13 and FIG. 14, the actuator 743 includes the prime mover 748 and a worm 749.

(Circular Disc Member)

As illustrated in FIG. 13 and FIG. 14, the circular disc member 9 includes a circumferential hole 91 and a gear part 92. The circumferential hole 91 is arranged on the outer periphery of the circular disc member 9 in the circumferential direction centering around the transferring member 71. The gear part 92 is arranged on the outer peripheral surface of the circular disc member 9 while meshing with the worm 749.

The guide pin 31 is fixed to the travel frame 3. The guide pin 31 is relatively movably engaged with the circumferential hole 91. The circular disc member 9 is configured so as to be capable of rotating centering around the transferring member 71 by engaging the guide pin 31 with the circumferential hole 91. When the worm 749 is rotated by the prime mover 748, the circular disc member 9 is rotated via the gear part 92 centering around the transferring member 71 onto the positions illustrated in FIG. 13 and FIG. 15.

An orthogonal hole 22 is arranged on the top 2 in the direction orthogonal to the Z direction. The transferring member 71 is engaged with the orthogonal hole 22 of the top 2 to be movable in the direction orthogonal to the Z direction. The base end of the link member 72 is axially supported on the circular disc member 9 by the pivot shaft 724 so as to be rotatable. The transferring member 71 is fixed to the front end of the link member 72.

(Control unit)

The control unit controls the actuator 743 as follows. That is, the control unit controls the actuator 743 such that the pivot shaft 724 and the transferring member 71 are positioned as illustrated in FIG. 13 when the top 2 is transferred in the Z1 direction to rotate the circular disc member 9.

As illustrated in FIG. 13, the transferring member 71 is arranged on the position in the X2 direction from the pivot shaft 724. In FIG. 13, the bias member 73 biases the top 2 in the Z2 direction via the transferring member 71 by biasing the link member 72 in the anticlockwise rotational direction. As described above, when the top 2 is transferred in the Z1 direction, it is possible to bias the top 2 in the Z2 direction.

In addition, the control unit controls the actuator 743 such that the pivot shaft 724 and the transferring member 71 are positioned as illustrated in FIG. 15 when the top 2 is transferred in the Z2 direction to rotate the circular disc member 9.

As illustrated in FIG. 15, the transferring member 71 is arranged on the position in the X1 direction from the pivot shaft 724. Also in FIG. 15, the bias member 73 biases the top 2 in the Z1 direction via the transferring member 71 by biasing the link member 72 in the anticlockwise rotational direction. As described above, when the top 2 is transferred in the Z2 direction, it is possible to bias the top 2 in the Z1 direction.

In other words, the biasing mechanism 7 of the third embodiment 3 includes: the transferring member 71 engaged with the top 2 such that the member 71 can transfer in the direction orthogonal to the Z direction; the circular disc member 9 provided to the travel frame 3 such that the member 9 is rotatable centering around the pivot shaft 724; the link member 72 having a base end and a front end, wherein the base end being axially supported on the circular disc member 9 by the pivot shaft 724, the transferring member 71 being fixed to the front end; the bias member 73 to bias the top 2 via the transferring member 71 by biasing the link member 72 in a specific rotational direction; and a switch unit to bias the top 2 in the direction opposite the transfer direction of the top 2 by rotating the circular disc member 9 such that, when the top 2 is transferred in one direction along the Z direction, the transferring member 71 is positioned in one direction orthogonal to the Z direction from the pivot shaft 724, and, when the top 2 is transferred in other direction along the Z direction, the transferring member 71 is positioned in the other direction orthogonal to the Z direction from the pivot shaft 724.

According to the third embodiment 3, the link member 72 becomes shorter than that of the first embodiment, allowing the width of the biasing mechanism 7 in the X direction to be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed:
1. A medical couch apparatus, comprising:
a couch body;
a top, on which a subject is mounted;
a frame arranged between the couch body and the top to be guided in the rostrocaudal direction of the subject by the couch body;
a driving unit configured to transfer the top in the rostrocaudal direction via the frame;
a guide unit arranged between the frame and the top and configured to guide the top in the rostrocaudal direction;
a biasing mechanism configured to bias the top in an opposite direction of a transfer direction of the transfer of the top; and
a bias control unit configured to apply a force to the top to be transferred in the opposite direction for the frame through the bias applied by the biasing mechanism when the transfer of the top by the driving unit is stopped, wherein
the biasing mechanism comprises:
a transferring member configured to engage with the top such that the transferring member transfers in the direction orthogonal to the rostrocaudal direction;
a link member having a center part that is axially supported by the frame rotatably and at opposite ends, the link member configured to guide the transferring member in a reciprocable manner between the opposite ends;
a bias member configured to bias the top via the transferring member by biasing the link member in a specific rotational direction; and
a switch unit configured to bias the top in the opposite direction by
transferring the transferring member to one of the opposite ends of the link member when the top is transferred in one direction along the rostrocaudal direction, and transferring the transferring member to another end of the opposite ends of the link member when the top is transferred in a direction opposite the one direction.

2. The medical couch apparatus according to claim 1, wherein the bias control unit comprises a binding unit configured to
  bind the top such that the top is not transferred in the opposite direction for the frame by resisting the bias applied when the top is transferred via the frame by the driving unit, and
  release a binding of the top such that the top is transferred in the opposite direction for the frame by the bias applied if the power source is interrupted by the switch.

3. The medical couch apparatus according to claim 1, wherein the binding unit comprises an electromagnet configured to
  bind the link member such that the link member is not rotated against the bias applied by attracting the link member when the power source is supplied, and
  release a binding of the link member when the power source is interrupted when the transfer of the top is stopped.

4. The medical couch apparatus according to claim 1, wherein the switch unit comprises:
  an engaging member that configured to engage with the couch body such that the couch body transfers in the rostrocaudal direction; and
  a juncture member having a lengthy shape, wherein
  the transferring member is provided at one longitudinal edge portion,
  the engaging member is provided at the other edge portion,
  the engaging member is configured to
    transfer the transferring member to the one of the opposite ends of the link member by the frictional force received from the couch body when the top is transferred in the one direction along the rostrocaudal direction, and
    transfer the transferring member to the another end of the opposite ends of the link member by the frictional force received from the couch body when the top is transferred in the direction opposite the one direction.

5. The medical couch apparatus according to claim 4, further comprising:
  a detecting unit configured to output signals when the transferring member is positioned at either one of the opposite ends of the link member; and
  an informing control unit configured to demonstrate the position of the transferring member based on the output signals.

6. The medical couch apparatus according to claim 1, wherein the switch unit comprises:
  an actuator configured to transfer the transferring member in a reciprocable manner between the opposite ends, and
  a control unit configured to control the actuator such that the actuator is configured to
    transfer the transferring member in the one direction when the top is transferred in the one direction along the rostrocaudal direction, and
    transfer the transferring member in the direction opposite the one direction when the top is transferred in the direction opposite the one direction.

7. The medical couch apparatus according to claim 6, further comprising:
  a detecting unit configured to output signals when the transferring member is positioned at either one of the opposite ends of the link member; and
  an informing control unit configured to demonstrate the position of the transferring member based on the output signals.

* * * * *